United States Patent [19]
Meyer et al.

[11] Patent Number: 5,956,139
[45] Date of Patent: Sep. 21, 1999

[54] CROSS-CORRELATION METHOD AND APPARATUS FOR SUPPRESSING THE EFFECTS OF MULTIPLE SCATTERING

[75] Inventors: William V. Meyer, Lakewood, Ohio; David S. Cannell, Santa Barbara, Calif.; Padetha Tin, Strongsville, Ohio; H. Michael Cheung, Hudson, Ohio; J. Adin Mann, Jr., Cleveland Heights, Ohio; Thomas W. Taylor, Cleveland, Ohio; James A. Lock, Cleveland Heights, Ohio; Jixiang Zhu, Bridgewater, N.J.; Anthony E. Smart, Costa Mesa, Calif.

[73] Assignee: Ohio Aerospace Institute, Brook Park, Ohio

[21] Appl. No.: 08/905,536

[22] Filed: Aug. 4, 1997

[51] Int. Cl.[6] ..................................................... G01N 21/00
[52] U.S. Cl. .......................... 356/338; 356/340; 356/343
[58] Field of Search .................................. 356/335–343; 250/574, 573

[56] References Cited

U.S. PATENT DOCUMENTS

| | | | |
|---|---|---|---|
| 4,804,853 | 2/1989 | Borden et al. | 356/343 |
| 4,978,863 | 12/1990 | Lyons et al. | 250/574 |
| 5,140,463 | 8/1992 | Yoo et al. | 356/337 |
| 5,198,369 | 3/1993 | Itoh et al. | 356/342 |
| 5,568,259 | 10/1996 | Kamegawa | 356/373 |
| 5,581,349 | 12/1996 | Halaka | 356/336 |
| 5,641,919 | 6/1997 | Dahneke | 356/336 |

OTHER PUBLICATIONS

Photon Correlation & Scattering, 1996 Technical Digest Series, vol. 14, Capri, Italy, Aug. 21–24, 1996.

Suppression of Multiple Scattering Using a Single Beam Cross–Correlation Method, published in Light Scattering and Photon Correlation Spectroscopy by Kluwer (Dordrecht), 1997.

*Primary Examiner*—Hoa Q. Pham
*Attorney, Agent, or Firm*—Vickers, Daniels & Young

[57] ABSTRACT

A method and apparatus for analyzing a fluid containing light scattering components. The apparatus includes a laser adapted to direct abeam of light into the fluid such as a liquid containing particles, and at least two detectors to receive light scattered by the fluid, which received light is used to calculate a physical property of the fluid. A focusing lens may be used to focus the light beam to a focal waist in the fluid to enhance the degree of spatial coherence of the scattered light. The two detectors are aligned onto the focal waist and are adapted to send a signal to a data processor which correlates the signal received from said two detectors. The two detectors are spaced a substantially equal distance from the focal waist and are oriented at substantially the same angle with respect to the direction of propagation of the incident beam. The data processor is adapted to cross-correlate the signals received from the two detectors. A polarizer can be positioned between the focal waist and the two detectors to aid in positioning the detectors and to enhance the efficiency and speed of the measurement.

45 Claims, 6 Drawing Sheets

CROSS-CORRELATION METHOD AND APPARATUS FOR SUPPRESSING THE EFFECTS OF MULTIPLE SCATTERING

FIELD OF THE INVENTION

The invention relates to the field of optical measurement of various types of media and in particular, relates to a method and apparatus for the measurement of physical properties of particle-containing media by use of dynamic light scattering; however, the invention has broader applications and can be used to measure a wide variety of physical properties of media, such as gas, liquid and solid media, which media contain a wide variety of substances, such as particles, colloids, compounds and the like. Although the invention has a broad range of applications, it will be described with particular reference to particle-containing media.

BACKGROUND OF THE INVENTION

Beginning with the advent of the laser, dynamic light scattering has proven to be an invaluable technique for determining the dynamic properties of a variety of systems. It has been used to study order-parameter dynamics near the critical points of both pure fluids and binary mixtures. It has proven to be the most accurate method known for determining the diffusion coefficient of macromolecules such as proteins and polymers, as well as that of other particles. Because the radius of a spherical particle can be determined from knowledge of its diffusion coefficient, dynamic light scattering has become an important tool for measuring the size of colloidal particles. It has been determined that light scattered from a collection of particles detected at a point in the far field fluctuates in time as the suspended particles diffuse. The time variation of the intensity of the detected light scattered can be correlated in time to produce an auto-correlation function which gives information concerning the diffusion coefficient of the particles which, in turn, depends upon the diameter of the particle. In practice, measurement of the auto-correlation function is an accurate and reliable method for determining the diffusion coefficient and the diameter of particles in highly dilute systems. In general, the method of dynamic light scattering can be used to measure the dynamic properties of many relatively transparent samples.

Although the use of an auto-correlated signal is known to be useful for highly dilute systems, it has been found that multiple scattering of light in many samples, including more concentrated colloidal suspensions, distorts the measured signal, thus, strongly biasing the determination of the dynamics or diffusion coefficient. For moderately strongly scattering samples, not all of the light scattered leaving the sample is the result of single scattering. Under these conditions, it can be difficult to interpret data in any reliable way. One exception to this situation occurs in the limit of extremely strongly scattering samples, where the photons can be treated as diffusing throughout the sample. In this case, it is possible under certain circumstances to deduce useful information regarding short time scale dynamics of the process giving rise to the scattering.

In an effort to overcome the problem of multiply light scattering, several strategies have been developed. These strategies include calculating the effects of multiple scattering when only few scatterings per incident photon occur, attempting to simulate, via computer, the effects of multiple scattering in the intermediate scattering regime, attempting to calculate the effects of multiple scattering in the diffusing photon limit, and attempting to find scattering geometries in which either multiple scattering or its effects are partially or totally suppressed.

Presently, the best results have been obtained by attempting to suppress the effects of multiple scattering. The most effective experimental method yet devised for dealing with multiple scattering is the cross-correlation technique invented by Phillies. The Phillies method relies on the fact that in order for the incident light to be scattered in a particular direction, the wave vectors of the incident and light scattered must be coupled by that of the dielectric constant fluctuation responsible for the scattering, in a Bragg-like relation, $k_{inc}=k_s \pm q$. Here $k_{inc}$ is the wave vector of the incident light, $k_s$ is that of the light scattered, and q is the wave vector of the fluctuation responsible for the scattering. Because of this Bragg condition, two different beam-detector combinations can be aligned so as to simultaneously collect light which has been scattered by the same fluctuation. Of course, the two detectors also collect light which has been multiply scattered. This results in detector signals $i_A(t)$ and $i_B(t)$ which arise from both single and multiple scattering contributions. The single scattering contributions are strongly correlated with each other at all times, while the multiple scattering components are only weakly correlated. Measuring the temporal cross-correlation function of the two detector outputs $<i_A(\tau)i_B(0)>$, then provides the same information as would be obtained in the single scattering limit using a conventional single-beam, single-detector arrangement to measure $<i(\tau)i(0)>$. Although this technique showed promise for determining particle diameters in concentrated solutions, the two-beam, two-detector scattering system is expensive and is difficult to align thereby minimizing the usefulness of such techniques in practice.

In view of the state of the art for determining the dynamic properties of various types of systems, there is a need for a simple, inexpensive and accurate method and apparatus for determining the physical properties of various systems, such as liquid systems having a variety of particle concentrations, and for measuring other types of systems which scatter light.

SUMMARY OF THE INVENTION

The present invention pertains to a new method and apparatus for measuring dynamic wave scattering which uses a single-beam, multiple-detector system to minimize multiple scattering problems and to provide accurate results for the dynamic properties of a variety of systems, such as liquid system containing particles, over a wide particle concentration range. The minimization and/or elimination of the multiple scattering effects from waves scattered by the particle-containing sample is accomplished by cross-correlating waves scattered from a single beam, such as a laser beam, which is detected by two or more detectors. As can be appreciated, the cross-correlation technique of the present invention is not limited to laser beams, visible light sources or the like. Any type of wave source can be used, including lasers, ultraviolet light, infrared light, ultrasonic waves, etc., and combinations thereof. In effect, the invention pertains to a method and apparatus for measuring a physical property of a sample by directing a single wave source into the sample, detecting at least a portion of the wave source which has been scattered by the sample, and processing the signal from multiple detectors to determine a physical property of the sample.

In a more specific aspect of the present invention, the apparatus incorporates a source of waves, such as a laser, which produces a beam. The beam is directed into a sample, such as a liquid containing particles. At least a portion of the waves scattered out of the incident beam by the sample is detected by two or more detectors, each of which produces a signal which varies in response to the intensity of the scattered wave source reaching a particular detector. A detector, such as a light detector, could consist of an optical fiber which receives at least a portion of the scattered wave source, such as a laser, and conveys the wave source to a sensor, such as a photo-multiplier tube, pulse counting avalanche photo-diode, or an analog solid state detector. The detectors are positioned such that waves singly scattered out of the wave source by the sample, and which reaches the detectors, produces detector output signals which are correlated with each other. In one such arrangement, two detectors are arranged so as to each collect a portion of the scattered waves lying in the same single scattering speckle or coherence area. In an alternative arrangement or an arrangement in addition to the one described above, the two or more detectors are arranged such that waves, such as light, which has been scattered by the sample multiple times produces detector output signals which are not or only weakly correlated with each other. In such an arrangement, the detectors are separated a sufficient distance from one another so that the separation distance is greater than the distance over which multiple scattering is spatially correlated in the direction of the detector's separation. Preferably, the detectors are positioned so as to collect singly scattered waves which is strongly correlated and be spaced a sufficient distance from one another so that multiply scattered waves are not or only weakly correlated. The positioning of the detectors in such a configuration is possible since a scattered wave source, such as light scattered from a liquid containing particles is not spatially uniform, but instead forms regions of coherent scattered waves, which regions are larger for singly scattered waves than for multiply scattered waves. In other words, singly scattered waves typically forms larger speckles or coherence areas than does multiply scattered waves. In effect, single scattering of waves from a sample originate from the region of primary illumination, such as the small cross section of a focused wave source while multiple scattering tends to arise from a larger fuzzy "halo" around the incident beam, thus appearing to come from a significantly larger source. Because the scattering arises from a spatially incoherent source, its spatial coherence properties are determined by the apparent dimensions of the source as viewed by the detector. Consequently, a singly scattered wave gives rise to scattering speckles or coherence areas which are typically much larger in one dimension than they are in another. The speckles formed by a singly scattered wave are large in the dimension in which the source appears small such as transverse to the incident wave source, and small in the dimension in which the source appears large, that is parallel to the incident wave source. Therefore, the speckle corresponding to single scattering has a high spatial coherence over a larger region than does the speckle corresponding to multiple scattering. Multiply scattered waves also give rise to speckles, but since the smallest source dimension for multiple scattering is larger than for single scattering, multiple scattering speckles are smaller than single scattering speckles in a direction which is non-parallel to the incident wave source. Therefore, it has been found that if a tightly focused wave source, such as a laser beam, of diameter d which passes through a sample produces scattered waves which can be correlated in a direction non-parallel to the wave source. By collecting the scattered wave source from two or more locations separated in a direction non-parallel to the wave source, it is possible to discriminate between singly scattered waves and multiply scattered waves by cross-correlating the two detector outputs. The method and apparatus can effectively determine the physical properties of samples having a particle size range of 10 angstroms to at least about 10 microns and more preferably a size range of 30 angstroms to 3 microns and can be used to analyze the physical properties of the sample over a wide range of particle concentrations. The physical properties that can be determined from the detected scattered waves include, but is not limited to, the size and/or distribution of sizes of particles in the sample, In accordance with yet another aspect of the present invention, the detectors are positioned in a region which is substantially transverse to the wave source, i.e. incident beam or wave. The direction which is transverse to the wave source is the direction in which the single scattering speckles are largest. In such a direction, the length of single scattering speckles is approximately calculated by $(\lambda/D_w)R$, wherein $\lambda$ is the wavelength of the wave source, $D_w$ is the width of the waist of the wave source, and R is the distance of the two detectors from the scattering volume. However, as can be appreciated, the detectors can be positioned at any region about the sample to detect the scattered wave source.

In accordance with still another aspect of the present invention, the method of analysis used to process the output of the multiple detectors can include analog cross-correlation and/or digital cross-correlation. Analog cross-correlation can be used to determine the temporal cross-correlation function $<i_A(t)i_B(t-\tau)>$, where $i_A(t)$ and $i_B(t-\tau)$ are the output signals of two analog detectors A and B at times t and t-$\tau$, respectively and the brackets < > denote time averaging. Digital cross-correlation can be used to determine the cross correlation function $<n_A(t)n_B(t-\tau)>$, where $n_A(t)$ and $n_B(t-\tau)$ are the number of detected pulses produced during a short period of time by detectors A and B during the time intervals centered on time t and t-$\tau$, respectively. Furthermore, the outputs of the detectors could be processed by measuring the cross spectral density of two or more signals $i_A(t)$ and $i_B(t)$ and/or the signal pulse streams $n_A(t)$ and $n_B(t)$.

In accordance with still yet another aspect of the present invention, the method and apparatus can be used in either auto-correlation mode or cross-correlation mode. Auto-correlation of the detected scattered wave source is accomplished by processing only the signal produced from a single detector. Cross-correlation of the detected scattered wave source is accomplished by processing data from two or more detectors. The switching between auto-correlation and cross-correlation can be accomplished by the connecting and/or disconnecting of the detectors, and/or by a hardware and/or software switch. As a result, the same apparatus can be used as either a conventional dynamic light scattering instrument, or used in the cross-correlation mode to suppress the effects of multiple scattering, as necessary. In samples, such as gasses or liquids containing wave scattering components such as particles, in which the particle concentration is sufficiently dilute so as to exhibit insignificant multiple scattering, conventional dynamic wave scattering (auto-correlation) can be selected since auto-correlation provides relatively rapid and accurate particle sizing for such systems. However, when multiple scattering becomes significant, as it typically does for all but the most dilute samples, cross-correlation is to be selected to suppress the multiple scattering. Because concentrated samples are often encountered in practice, and because dilution of the samples is not always feasible or desirable, the use of auto-correlation is severely limited., but cross-correlation can be used to accurately and rapidly determine various physical properties of such samples.

In accordance with another aspect of the present invention, the detectors can be any arrangement which produces an output signal that varies in response to the intensity or power reaching the detector. In addition, such devices can be fabricated so as to accept only a portion of the scattered wave reaching a given area. Such modification of the amount of scattered wave reaching the detectors can be accomplished by the use of lenses, mirrors, various apertures, and/or polarizers which can be used to restrict the accepted portion of the wave to that which originates from a region in the sample. Such a region can be, but is not required to be, the region illuminated by the incidence beam. In addition or alternatively, the restricting of the amount of scattered waves reaching a detector can be achieved by using optical fibers, either single- or multi-mode optical fibers in conjunction with lenses, either conventional or gradient lenses.

In accordance with yet another aspect of the present invention, the wave source beam is focused to a relatively narrow waist within the sample. The focusing of the beam results in the desirable effect of increasing the distance over which single scattering is correlated without significantly affecting the distance over which multiple scattering is correlated. The focusing of the wave source beam enhances the size of single scattering speckles while having little effect on the size of multiple scattering speckles. Preferably, the detectors are positioned to detect singly scattered wave emanating substantially from the narrow waist of the wave source.

In accordance with still another aspect of the present invention, a polarizer is positioned between the detectors and the sample during positioning of the detectors and/or during operation of the detectors. A large number of samples produce polarized singly scattered waves. In fact many samples produce highly polarized singly scattered waves and weakly polarized multiply scattered waves. When positioning the detectors, the polarizer is used to block the singly scattered waves. Once the singly scattered waves are blocked by the polarizer, the detectors are spaced apart until the detector outputs do not correlate or minimally correlate the scattered waves detected by the detectors. Once the desired spacing of the detectors is obtained, the polarizer is removed or repositioned to allow the singly scattered waves reach the detectors. By using a polarizer to position the detectors, the detectors can be properly spaced apart to limit or eliminate the signal caused by multiply scattered waves. Thus, the correlated data received from the detectors will be or essentially will be caused by detection of singly scattered waves by the sample. If the polarizer is maintained in position between the sample and the detectors, the polarizer also acts as a filter to eliminate at least a portion of the multiply scattered waves. Multiply scattered waves is only partially polarized. The use of a polarizer effectively screens out a substantial amount of multiply scattered waves thus further reducing the amount of noise created by the detection of multiply scattered waves by the detectors.

In accordance with still yet another aspect of the present invention, the sample is placed within a sample container which is adapted to hold the sample in position so that the wave source can be passed through the sample. Preferably the sample container is substantially transparent so as not to interfere with the wave source. A polished surface may be included on the sample container so as to further reduce the distortion of the wave source as it passes through the sample container. An index matching container may also be used to reduce parasitic scattering and to compensate for the index of refraction of the sample. If an index matching container is used, the index matching container is filled with an index matching fluid and the sample is placed within the index matching container and is at least partially immersed into the index matching fluid. The index matching container may also include polished surfaces to reduce the distortion of the wave source as it passes through the index matching container.

In accordance with still another aspect of the present invention, the detectors are spaced an substantially equal distance from the wave source in the sample.

In yet another aspect of the present invention, the detectors are all aligned on substantially the same point on the wave source in the sample.

The primary objective of the present invention is to provide a method and apparatus for simply and accurately analyzing one or more properties of the sample by analyzing scattered wave source from the sample.

Another object of the present invention is to provide a method and apparatus that directs a single wave source, such as a laser, into a sample, such as a liquid containing particles, and detecting at least a portion of the scattered wave source from the sample by two or more detectors, cross-correlating the detected wave source to determine one or more properties of the sample.

Still another object of the present invention is to provide a method and apparatus for directing a wave source into a sample and detecting at least a portion of the scattered waves from the sample by two or more detectors and cross-correlating the detected scattered waves to suppress the detected multiply scattered waves and to determine one or more properties of the sample by analyzing the detected singly scattered waves.

Yet another object of the present invention is to space the multiple detectors from one another such that the detectors strongly correlate singly scattered waves and only weakly or not at all correlate multiply scattered waves from a sample.

Yet still another object of the present invention, the detectors are spaced from one another a sufficient distance to only weakly or not at all correlate multiply scattered waves and spaced sufficiently close together to be positioned within a single speckle of a singly scattered waves.

Another object of the present invention is the use of lenses, mirrors, apertures, polarizers and the like to restrict detected scattered waves to only scattered waves originating from a well defined region in te sample, to restrict the detection of a portion of multiply scattered waves, and/or to position the detectors.

Still another object of the present invention is the use of detectors having single- or multi-mode optical fibers in conjunction with lenses to restrict detection of scattered waves to only scattered waves originating from a well defined region in the sample.

Still yet another objective of the present invention is to focus the wave source in a sample to increase the size of speckles of singly scattered waves.

Another object of the present invention is to use a polarizer to position the multiple detectors prior to analyzing the detected scattered waves for one or more properties of the sample.

Still another object of the present invention is an apparatus which has multiple modes of operation including the mode of auto-correlation and the mode of cross-correlation of information received from one or more of the detectors.

These and other objectives and advances will become apparent to those skilled in the art upon reading the following descriptions together with the accompanying drawings.

BRIEF DESCRIPTION OF THE DRAWINGS

Reference may now be made to the drawings, which illustrate various embodiments that the invention may take in physical form and in certain parts and arrangements of parts wherein.

DETAILED DESCRIPTION OF THE PREFERRED EMBODIMENTS

Figure 1A:
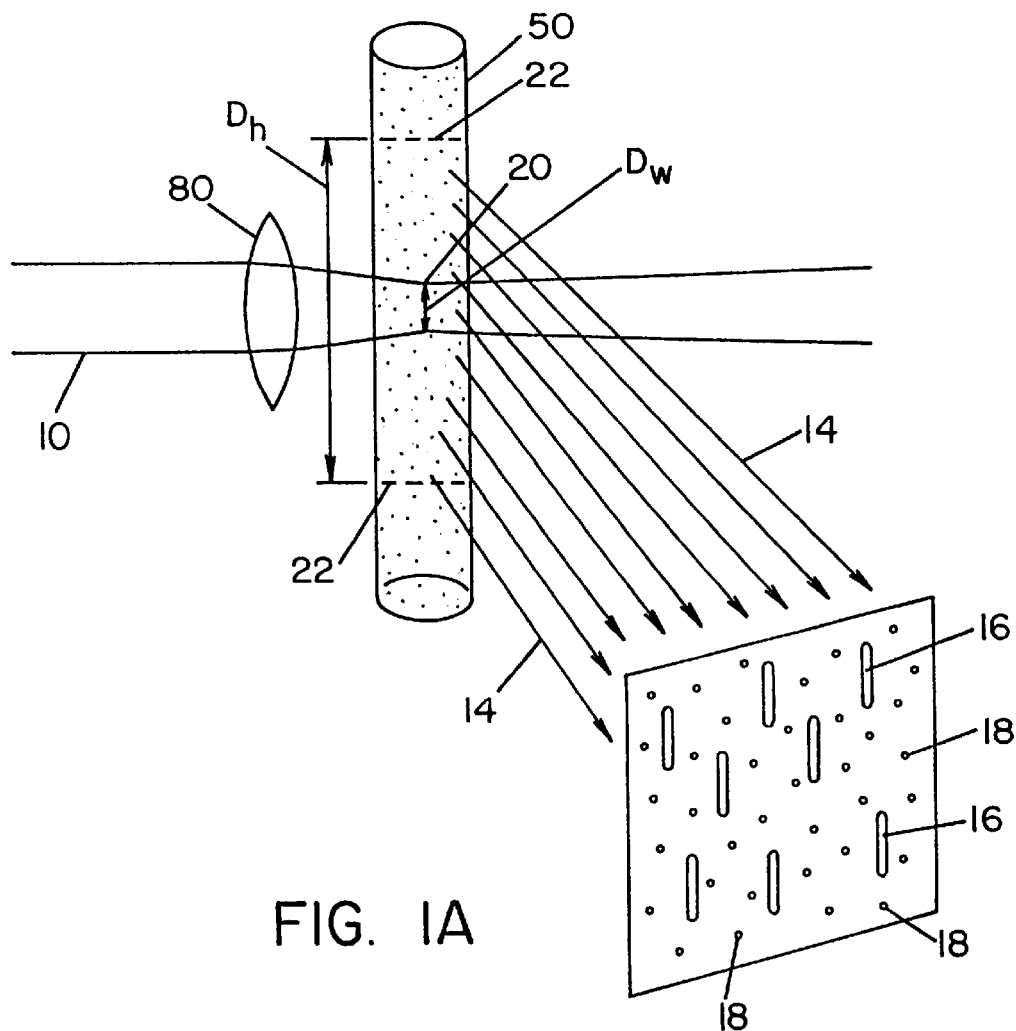
FIGS. 1A–1C illustrate the scattering of a focused source wave passing through a sample containing particles and the formation of single and multiple scattering speckles, the positioning of detectors within a single scattering speckle and the use of a polarizer to position the detectors.

Referring now to the drawings, wherein the showings are for the purpose of illustrating the preferred embodiments of the invention only and not for the purpose of limiting the same, in FIG. 1A, laser beam 10 is directed toward sample cell 50 which contains a sample consisting of a liquid in which particles are suspended. The laser beam is focused by a focal lens 80 thereby producing a focal waist 20 in sample cell 50. $D_w$ represents the width of focal waist 20. As laser beam 20 passes though the liquid containing particles, a halo 22 is formed about laser beam 10. The halo is caused by multiple scattering of the light from the laser beam by the sample. $D_h$ represents the width of halo 22. $D_w$ is much smaller than $D_h$. FIG. 1A also illustrates scattered light 14. Scattered light 14 includes both singly scattered waves and multiply scattered waves. The singly scattered waves are light from the laser beam that was scattered a single time in the sample before exiting sample cell 50. The multiply scattered light is light that was scattered multiple times in the sample before exiting sample cell 50. The light that is scattered is not spatially uniform in its intensity, but instead forms speckles or coherence areas of light 16, 18 and dark areas between the speckles. The speckles change with time getting brighter and then fading out and then reappearing once again in different positions as the particles diffuse in the sample. As shown in FIG. 1A, the larger speckles 16 are formed by singly scattered light and the smaller speckles 18 are formed by multiply scattered light. The height of speckles 16, 18 are a function of the wave length λ of laser beam 10, the distance R from the region of light scattering, and the width $D_w$ of the laser beam in the sample. The height of speckle 16 formed by single scattering is approximately equal to $(\lambda/D_w)R$ and the height of speckle 18 formed by multiple scattering is approximately equal to $(\lambda/D_h)R$. Since $D_w$ is much smaller than $D_h$, the height of speckle 16 is much larger than the height of speckle 18. As can be appreciated, the height of speckle 16 can be increased by narrowing the focal waist of laser beam 10 (decreasing $D_w$ specifically). It has been found that the narrowing of the focal waist of laser beam 10 does not substantially change the width of halo 22, thus the height of speckle 16 can be significantly changed by narrowing focal waist 20 without substantially changing the height of speckle 18.

Figure 1B:
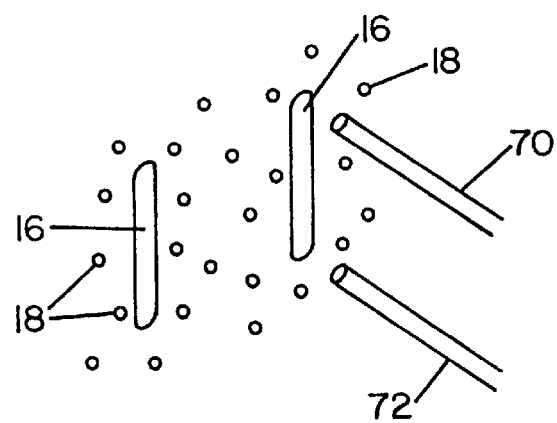
Figure 1C:
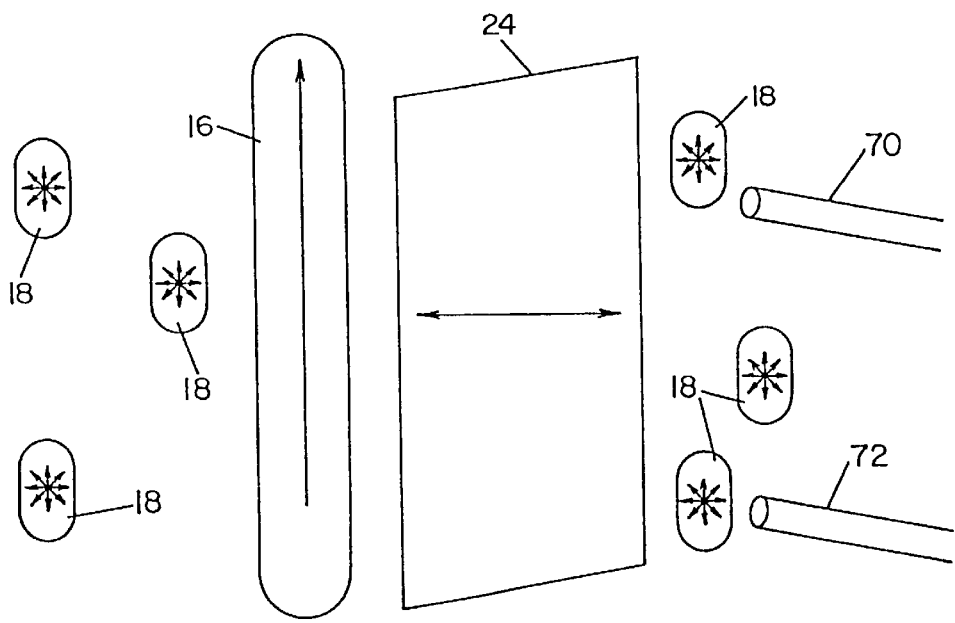

Referring now to FIGS. 1B and 1C, detectors 70, 72 are positioned to detect singly scattered light in speckle 16. The detectors 70, 72 are spaced close enough to one another so as to receive singly scattered light within a single speckle 16, but spaced a sufficient distance apart so the detectors do not detect multiply scattered light within a single speckle 18. It has been found that most singly scattered light is highly polarized in a single direction, but multiply scattered light is not. Therefore, the detectors 70, 72 can be positioned by using a polarizer as shown in FIG. 1C. As shown in FIG. 1C, singly scattered light speckle 16 is highly polarized in the direction indicated by the arrow (linearly polarized). Multiple scattering speckles 18 are shown to consist of light that is not linearly polarized. During the positioning of the detectors, polarizer 24 is positioned between speckles 16, 18 and detectors 70, 72. The polarizer is turned until the polarizer blocks all or a significant portion of the scattered light of speckle 16. Since the multiply scattered light is not linearly polarized, polarizer 24 does not completely block speckles 18. While the polarizer is blocking singly scattered light (speckle 16), the detectors are moved apart until both of the detectors do not detect or substantially do not detect light scattered within a single multiply scattered light speckle 18. In this manner, the extent to which multiply scattered light is correlated by detectors 70, 72 is significantly reduced thereby increasing the accuracy, efficiency and/or speed of measurements. As can be appreciated, polarizer 24 can be used during the measurement of the properties of the sample. If the polarizer is used, the polarizer in turned until the polarized light of speckle 16 can pass through the polarizer. Although the polarizer cannot completely screen all unwanted multiply scattered light, the polarizer does screen off some of the multiply scattered light thus potentially increasing the speed, efficiency and/or accuracy of measurement of the properties of the sample. The adjustment of the spacing of detectors 70, 72 is significantly easier, with or without using the polarizer, as compared with past alignment procedures using two different lasers and two detectors. Typically the time to properly position the detectors for the apparatus of the present invention is less than ten minutes.

Figure 2:
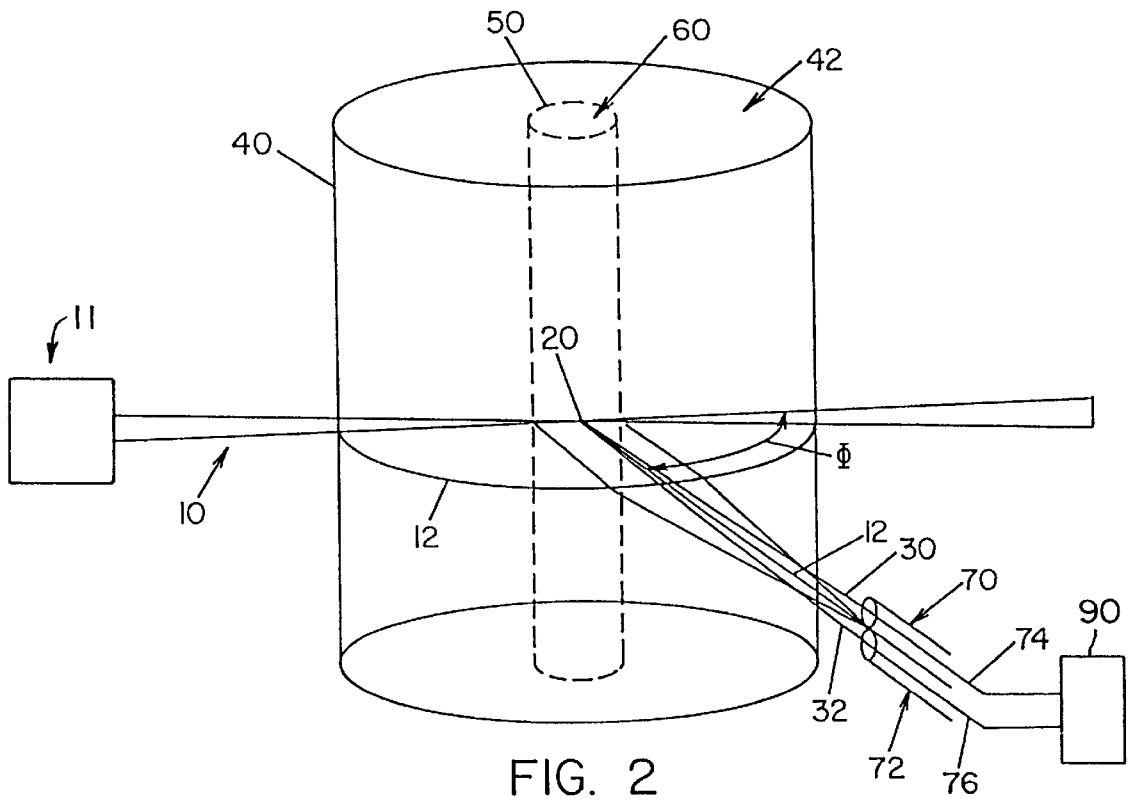
FIG. 2 is a graphical representation of the multiple scattering apparatus illustrating the two detectors aligned at substantially the same position on the focal waist of the source wave.

Referring now to FIG. 2, laser beam 10 from source 11 is directed toward an index matching vat 40 which contains an index matching liquid 42 and sample cell 50. Sample cell 50 contains a suspension 60 of small particles which particles are to be analyzed to determine the average diameter of the particles. Two detectors 70, 72 are illustrated to be in position above and below the plane 12 which plane is that which is perpendicular to the direction of polarization of the laser beam 10 and in which plane laser beam 10 lies. Preferably, the two detectors 70, 72 are aligned on the focal waist 20 and are aligned with scattered wave vectors 30, 32 respectively. Laser beam 10 is shown as being focused into a focal waist 20. The focusing of laser beam 10 can be accomplished by using a focusing lens or mirror, not shown.

FIG. 2 also illustrates the index matching vat 42 causing the light scattered at a given angle with respect to the direction of propagation of the wave source to focus on the line along which the detectors are placed. The focusing of the light scattered by the index matching vat causes more photons to be detected by the detectors thus increasing the efficiency and speed of the measurement. The information recorded by the two detectors is transmitted via paths 74, 76 to data processor 90 cross-correlated and the average particle diameter of the particles in the sample cell is calculated.

OPERATION OF THE APPARATUS

The specific operation of the apparatus will now be described. A sample cell which is preferably a transparent glass container test tube having an inner diameter of 10.1 mm and an outer diameter of 11.6 mm is selected, however, other dimensions or materials for the sample cell may be used. The sample cell is held rigidly on the axis of the transparent glass cylindrical index matching vat 40. The index matching vat contains an index matching fluid such as water or decalin. The index matching vat has an inner diameter of 80 mm and an outer diameter of 84.6 mm; however, the dimensions of the index matching vat are not limited to such dimensions. The glass sample cell and glass index matching vat create only a small effect on the behavior of the laser beam. The effect on the laser beam can be diminished by polishing a small flat surface on the sample cell and/or the index matching vat.

The laser beam is produced by an argon-ion laser having a vacuum wavelength of 514.5 nm. The laser beam is brought into focus by using a lens of focal length of 100 mm to form a focal waist diameter ($e^{-2}$) of about 88 um. As can be appreciated, other types of laser beams and different wavelengths can be used. In addition, other types of focusing lenses and/or mirrors may be used or can be completely eliminated. Furthermore, other waist diameters may also be used effectively.

As illustrated in FIG. 2, the focal waist 20 is located substantially at the center of sample cell 50, crossing the sample cell horizontally, perpendicular to the vertical axis of the sample cell. The laser beam enters the index matching vat preferably through a small, polished, flat area not shown, so as to preserve the circular symmetry of the beam. The light scattered resulting from the laser beam contacting the particles within the sample cell is collected by two detectors 70, 72. The detectors include two optical fibers with cores 74, 76, which are single mode for 633 nm. However, different optical fibers, either single- or multi-mode, can be used. In addition, the detectors do not have to involve optical fibers, but can be any type of light detector. The two ends of the fibers are polished, but need not have any special optical arrangement. The cores of the fibers are separated by approximately 0.25 mm. The ends of the two fibers were spaced from the focal waist at approximately 170 mm. This distance of the detectors is selected since at such distance from the focal waist, the largest amount of light scattered, at a given scattering angle, leaving the sample cell is brought into an approximate vertical line of focus by refraction of the outer surface of the index matching vat as shown in FIG. 2. In addition lenses, mirrors, apertures, etc., can be used alone or in conjunction with optical fibers to define the exact portion of the sample volume from which the light scattered is accepted in order to be detected.

The 0.25 mm spacing of the two detectors is also selected to be within the calculated size of a speckle for singly scattered light. The size of a speckle for singly scattered light for a specific system is approximately equal to the wavelength of the light beam divided by the diameter of the light beam at the focal waist multiplied by the distance of the detectors from the focal waist. In the present system, the size of the single scattering speckle is on the order of approximately one millimeter ((0.5145 $\mu$m/88 $\mu$m)170 mm≈1 mm) and the spacing of only 0.25 mm of the two detectors is sufficiently small enough to collect light within one speckle of singly scattered light.

One detector is positioned such that it is above the horizontal plane containing the laser beam and the other detector is positioned below the horizontal plane containing the incident beam. However as can be appreciated, the two detectors can be both positioned above or below the horizontal plane of the laser beam. It was also found that by positioning the detectors slightly above or slightly below the horizontal plane of the laser, the flare effects of multiple internal reflections resulting from the laser beam contacting the sample cell and/or index matching vat are significantly reduced. It was further found that the flare effect resulted in more problems as the concentration of the particles in the sample cell decreased.

In FIG. 2, the angle of the detectors with respect to the direction of propagation of the laser beam is illustrated by $\Phi$. It was found that samples which exhibit multiple scattering reveal an apparent narrow line source (singly scattered light emerging directly from the beam itself) lying within a much larger and more diffuse region. This diffuse source is light which has been scattered out of the illuminating beam and has subsequently been scattered one or more additional times. Since this source appears larger than the illuminating beam, the speckle it generates is much shorter vertically than the 0.25 mm separation of the fibers and thus contributes little to the cross-correlation of the signals generated by the two detectors. Because both the singly and multiple scattering sources have about the same dimension parallel to the incident beam, there is little or no discrimination against multiple scattering when the fibers were separated parallel rather than transverse to the beam. The light collected by each fiber of the detectors is delivered to an actively quenched silicon avalanche photo diode capable of single photon counting. These detectors produce approximately 10 nanosecond TTL-level pulses at rates proportional to the instantaneous optical power reaching each detector. The resulting pulse streams $n_A(t)$ and $n_B(t)$ were fed to a digital correlator which computed either the temporal auto-correlation function $$G(\tau) = <n(t)n(t-\tau)> \qquad (1)$$

for either pulse stream, or the temporal cross-correlation function $$G_{AB}(\tau) = <n_A(t)n_B(t-\tau)> = <n_B(t)n_A(t-\tau)> \qquad (2)$$

for both.

The correlator measures the number of counts received during each interval (t, t+T), which is denoted by n(t) in equations 1 and 2. By simultaneously forming the products of the current n value and the n values corresponding to 256 different delay times $\tau$, and accumulating these products for a sufficient time, an acceptably accurate measurement of either $G(\tau)$ or $G_{AB}(\tau)$ can be formed.

Two samples with different diameter particles were tested, namely 107 nm and 204 nm polystyrene latex spheres. The particles were placed in distilled water and concentrations in the range from 0.0017 wt % to about 5 wt % were tested. The sample cells were sealed to prevent dust particles from contaminating the sample. The index matching fluid was distilled water to match the index of refraction of the fluid in the sample cell; however, other index fluids could have been used which had a different index of refraction from the sample cell fluid. The particle diameters were initially measured using dynamic light scattering with conventional optics in highly dilute suspensions to verify the particle diameter of the samples. In such dilute suspensions, multiple scattering is essentially absent. Samples of different concentration were prepared by diluting a suspension of polystyrene latex spheres, applied at a nominal concentration of 10 wt %, determined by the manufacturers by evaporation to dryness and stated to vary as much as ±10%. The dilutant of distilled water was filtered to reduce dust. It was not found necessary to further filter the samples after dilution. The specimen tubes were rinsed with similarly filtered water before charging and sealing the specimen tubes with parafilm to prevent dust contaminating the samples.

Figure 3:
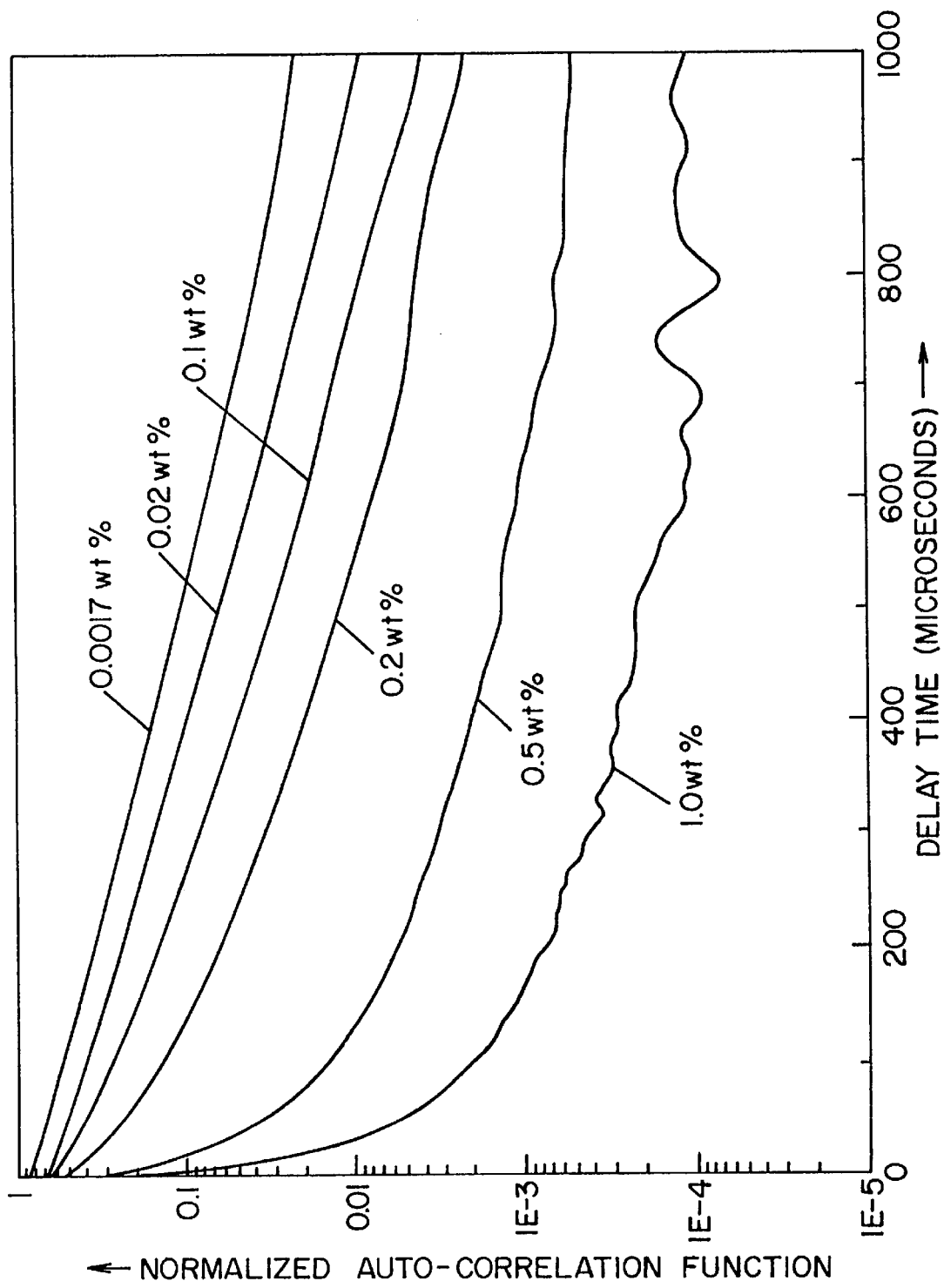
FIG. 3 is a graphical depiction of the normalized autocorrelation functions for increasing concentrations of 0.107 μm diameter polystyrene spheres in water.

FIGS. 3 through 6 disclose the results of measuring samples containing #107 nm diameter spheres over a wide variety of concentration ranges. FIG. 3 illustrates normalized auto-correlation functions for increasing concentrations of 107 nm polystyrene latex spheres in distilled water. The measurements were made at a 90° scattering angle ($\Phi=90°$) using one of the two optical fibers to collect the light scattered. The experiment was begun by measuring a series of single detector auto-correlation functions for samples of various concentrations, each measurement being accumulated for 300 seconds. For dilute suspensions, ranging from 0.0017 wt % to about 0.05 wt %, it was found that the normalized correlation function $G(\tau)$ was substantially exponential as exemplified by the uppermost two curves in FIG. 3. The results for the normalized auto-correlation function $[G(\tau)/B-1]$ versus delay time $\tau$, are shown in a semi-log. plot in FIG. 3 for six different concentrations. The plot in FIG. 3 was prepared by normalizing each measured correlation function by dividing it by the baseline B determined from the totals of the counts received during the processing run. Deviations from purely exponential decay which exponential decay results in a straight line on such a semi-log plot became more and more apparent for higher concentrations as illustrated in FIG. 3. The rapid initial decay followed by a much more slowly decaying tail evident in the auto-correlation function is noteworthy for the most concentrated samples. Auto-correlation functions with this general shape are commonly observed from strongly scattering samples approaching the diffusing photon limit. To quantify the turbidity of the samples, a power meter was used to measure the fraction of the incident beam power transmitted through the 10.1 mm samples. The results show that samples with concentrations in excess of about 0.2 wt % transmit an unscattered fraction of the incident beam of less than 0.6% and this fraction reduces more steeply still at higher concentration. Because of the extremely strong scattering exhibited by samples with concentration in excess of about 0.1 wt. %, the auto-correlation functions shown in FIG. 3 strongly deviate from single exponential decay. This is a direct consequence of collecting light which has been scattered more than once before leaving the sample. Each such scattering process significantly broadens the spectrum of light scattered, producing a rapid initial decay of the measured correlation function.

Figure 4:
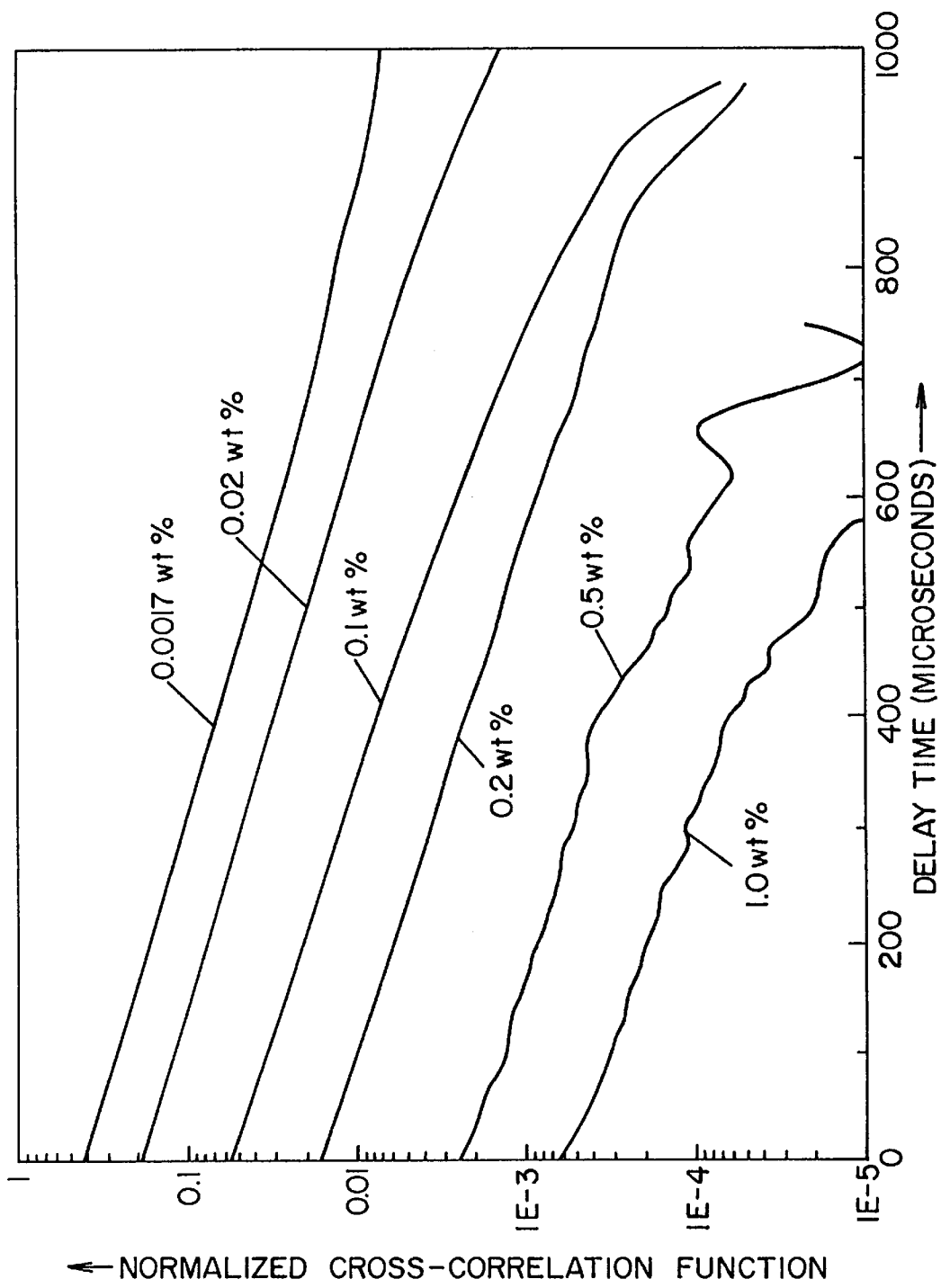
FIG. 4 is a graphical depiction of the normalized cross-correlation functions for increasing concentration of 0.107 μm diameter polystyrene spheres in water.

Cross-correlation functions $G_{AB}(\tau)$ were obtained for the same samples to determine the extent to which spatial cross-correlation reduces the unwanted effects of multiple scattering. The results of the cross-correlation experiment is illustrated in FIG. 4. The measurements shown in FIG. 4 show $[G_{AB}(\tau)/B-1]$ versus $\tau$ on a semi-log plot. Because the decaying portion of $G_{AB}(\tau)$ is only a small fraction of the baseline B for the cross-correlation data, especially for higher concentration samples, B was determined for each data set by fitting to a single exponential decay plus a baseline. As illustrated in FIG. 4, the curves of $[G_{AB}(\tau)/B-1]$ are essentially all linear and illustrate that the cross-correlation data for all the concentrations measured were consistent with single exponential decay. This result is in marked contrast with the results of the auto-correlation measurements shown in FIG. 3. As expected, dilute samples gave accurately exponential cross-correlation functions, as demonstrated by their linearity on a semi-logarithmic plot. However, the high-concentration samples also exhibited the same linear behavior and slope as those with low-concentration. Thus the data demonstrate that the simple artifice of spatial cross-correlation is adequate to permit useful dynamic light scattering measurements, even for samples which scatter so strongly that the probability of a photon traversing the sample without being scattered is only about one in $10^6$. More singly scattered photons are seen at larger scattering angles because of scattering near the edge of the cell and collecting ability of the cell geometry. FIG. 4 also illustrates that at the low concentration limit, the intercept of $G_{AB}(\tau)$, with $\tau=0$ for the cross-correlation functions does not exceed 0.42 whereas the intercept for the auto-correlation function approached unity. This result will always occur even in the absence of multiple scattering since the product of the scattered intensity at two different points (cross-correlation intercept) is always less than the square of the intensity at a given point (auto-correlation intercept) because the speckle field comprising the light scattered has less than perfect spatial correlation. The intercept value of the measured cross correlation functions decreased strongly with increased sample concentration thereby falling from about 0.42 for dilute samples to about $2.5\times10^{-3}$ for the 0.5 wt % sample and to only about $7\times10^{-4}$ for the 1.0 wt % sample. As the data shows, multiple scattering contributes very little to the cross-correlation function. Thus, of the light scattered by the 0.5 weight percent sample and collected by either fiber, only about 8% was singly scattered, and thus about 92% was multiply scattered. One obvious consequence of using cross-correlation functions is that to preserve measurement accuracy, the assessment of the baseline becomes more critical as the intercept reduces and thereby may require longer observation times.

Quantitative analysis of the data was performed on the measured cross-correlation and auto-correlation functions by the two cumulant equation $$G_A(\tau)=A \exp [-2(k_1 \tau - \{k_2/2\}\tau^2)]+B \qquad (3)$$

with A, B, $k_1$ and $k_2$ being adjustable. The first cumulant was related to an effective diffusion coefficient D, by $$k_1=Dq^2 \qquad (4)$$

where q is the scattering wave-vector given by $$q=(4\pi n/\lambda) \sin (\Phi/2) \qquad (5).$$

In the equations, n is the refractive index of the liquid in the sample cell and $\Phi$ is the scattering angle. An apparent particle diameter is calculated from $$D=k_b T/6\pi\eta\alpha \qquad (6)$$

where $k_b$ is the Boltzmann's constant, T is the absolute temperature, $\eta$ is viscosity and $\alpha$ is the apparent particle radius.

Figure 5:
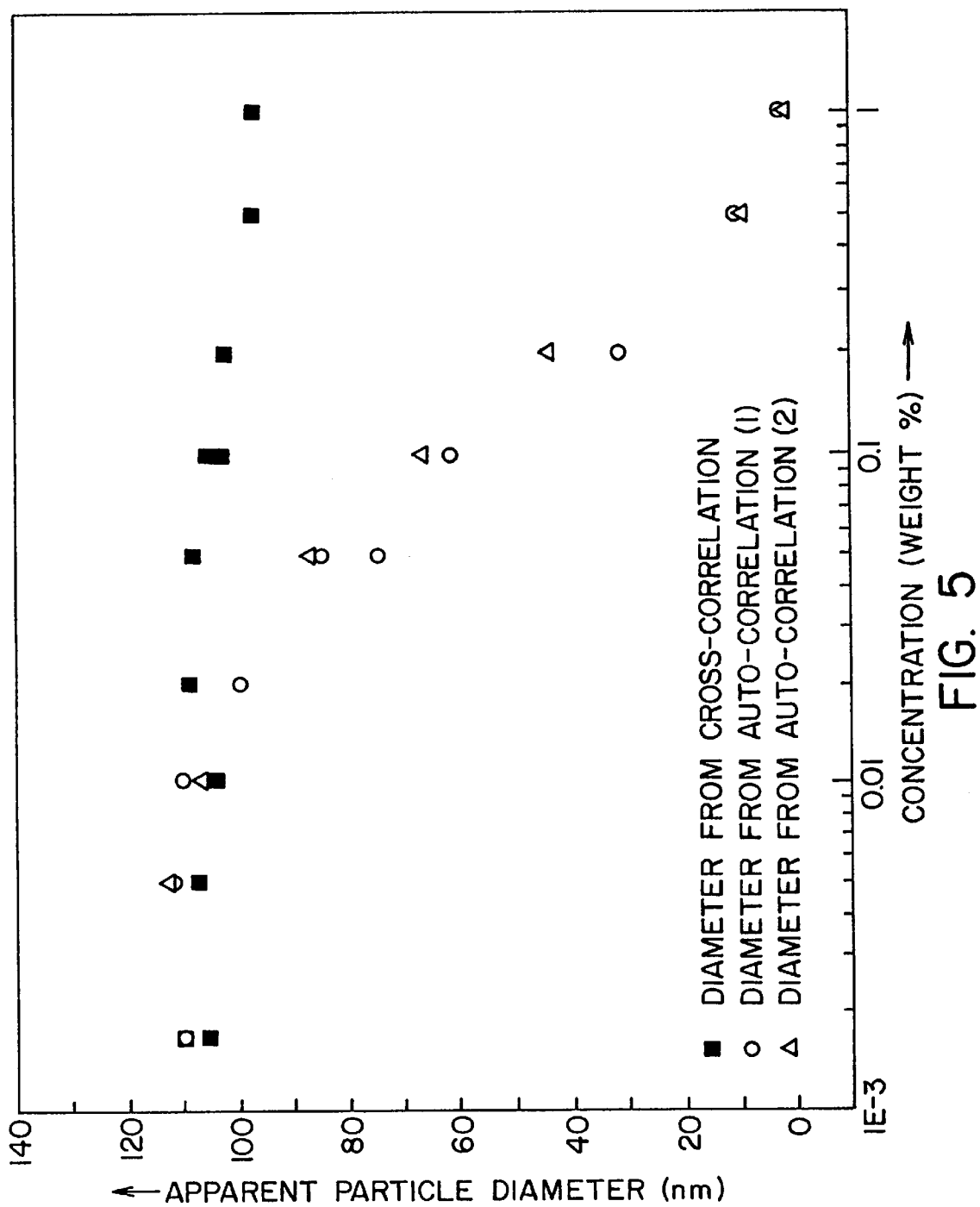
FIG. 5 is a graphical representation of the calculated diameter values of 0.107 μm polystyrene spheres in water measured at increased concentration by a cross-correlation technique and an auto-correlation technique.

The results of the analysis are summarized in FIG. 5 which presents the apparent particle diameter versus sample concentration derived from both the auto-correlation and cross-correlation functions. The results from auto-correlation and cross-correlation agree reasonably well at the lowest concentration, but substantially deviate for higher concentration samples. FIG. 5 illustrates that multiple scattering can severely distort the auto-correlation function data thus resulting in apparent particle diameters which deviate from the actual diameter by several orders of magnitude. Specifically, the results obtained by auto-correlation measurements begin to deviate systematically from the proper value when the sample concentration exceeds about 0.01 wt %. This deviation becomes dramatically more significant as concentration increases further. The measurement obtained using cross-correlation showed hardly any such tendencies thereby illustrating the usefulness of such a technique, even for higher particle concentration in suspensions.

Figure 6:
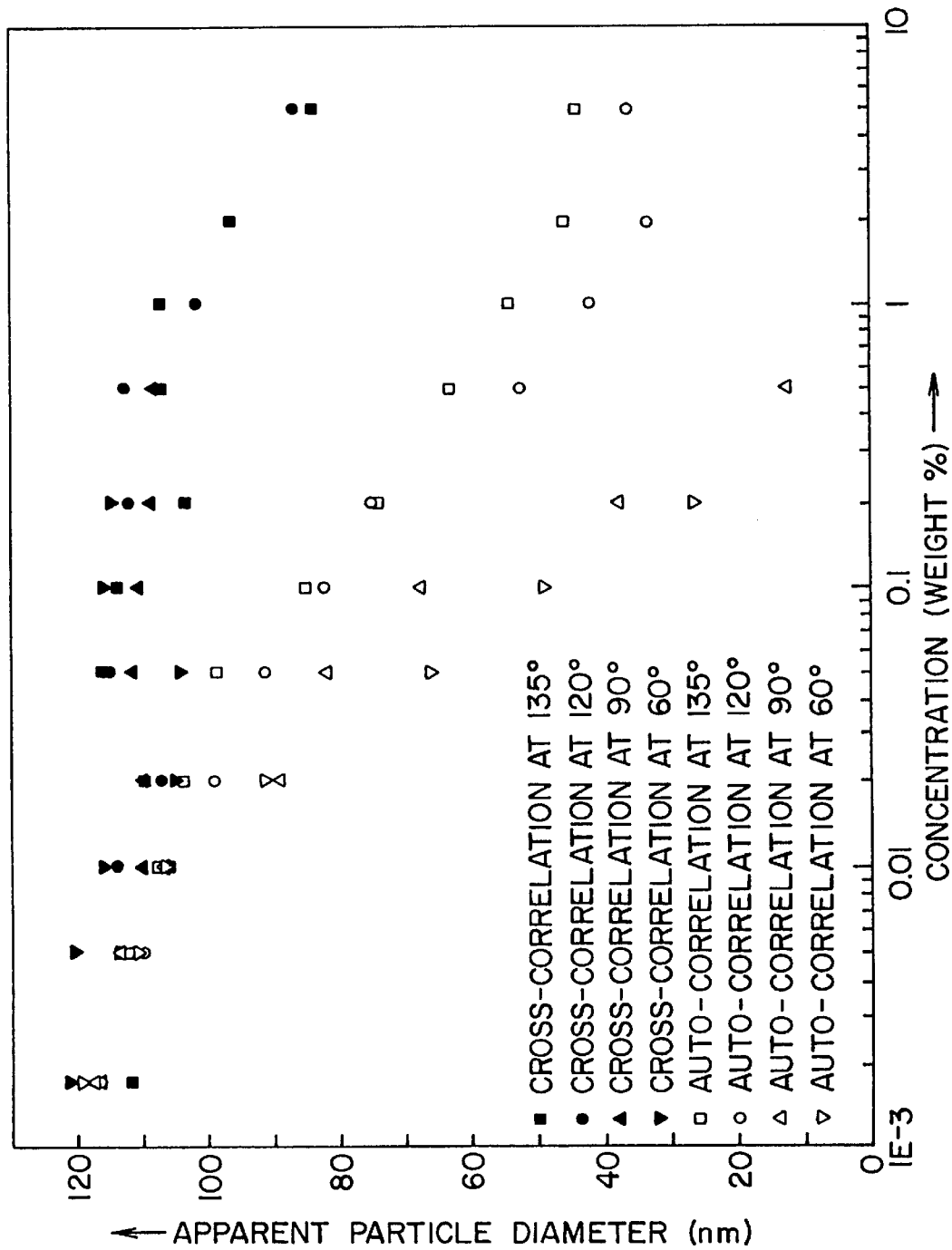
FIG. 6 is a graphical representation of the particle diameter inferred from auto and cross-correlation functions for measurements made by the detectors at scattering angles of 60°, 90°, 120° and 135°.

Referring now to FIG. 6, comparisons between the auto-correlation function and cross-correlation function at angles other than 90° were conducted. The particle size of the polystyrene spheres used was 107 nm and scattering angles of 60°, 90°, 120° and 135° were used. The data were analyzed by fitting the correlation function using equation 3. The values of the diameter inferred from the auto-correlation function are severely influenced by multiple scattering for the higher concentration samples. The results are also dependant on the scattering angle, yielding a systematic underestimate of the particle size which gets increasingly worse as the angle is moved more to the forward direction. In contrast, the values of the diameter inferred from the cross-correlation function show no systematic dependence on the scattering angle even at the highest concentration. The test was duplicated for 214 nm size particles. The results were similar to those for the 107 nm particles in that the auto-correlation function severely deviated from accurate measures at higher concentrations, but the cross-correlation function accurately determined the particle size at a wide range of concentrations.

The data in FIG. 6 demonstrate that spatial cross-correlation can be used to discriminate singly from multiply scattering in making dynamic light-scattering measurements to infer diameter of the particles within a fluid medium. The data in FIG. 6 also illustrate that the scattering angle selected for the detectors is not limited to a specific angle for cross-correlation.

The alignment of the detector fibers was also found to be quite tolerant of the goniometer angle and incident beam placement, but more critical with respect to the rotation of fiber retention assembly to place the fiber cores in the vertical direction aligned with the speckle elongation. Simple collection devices consisting of adjacent bare fibers without focusing lens were used in the experiment. The results indicate that bare optical fibers used as collection outputs do not limit the spatial regions from which the scattering is collected as narrowly as do conventional optics. The fibers were found to accept all light within their numerical aperture, typically about 0.1 for single mode fibers. Each fiber collected light from along the entire sample, which is not the most efficient way to selectively discriminate against multiply scattered light. An improved design would be to use focal lenses to restrict the accepted light to that originating in a localized portion of the sample. However, using bare fibers has the advantage of being extremely easy and also cost efficient. Although both conventional optics and the arrangement used in the experiment channel light scattered at a given angle to a detector, it is usual for conventional collection optics also to restrict physical length and height of the region from which light may be observed. Thus, well designed conventional optics can discriminate against multiple scattering somewhat better than bare fibers, for this reason alone. Nevertheless, it is well recognized for samples which transmit less than 10% of the incident beam, significant multiple scattering is collected even by conventional optical arrangements, with concomitant distortion of measured auto-correlation functions. Thus, it was found that spatial cross-correlation, even with non-discriminatory collection optics, can give reliable correlation functions for samples transmitting less than 1 part in a million of the incident beam. Under conditions of strong attenuation, as with more concentrated samples, the optical geometry collects singly scattered light preferentially from where the beam enters the cell rather than as conventionally from the center cell. This happens because the geometry collects light scattered at an angle to the beam, regardless of where along the beam path the scattering occurs, except for some small effects of optical aberrations in the cylindrical container and vat. For highly turbid samples, this overwhelmingly favors the single scattering events for which the total distance traveled in the sample before and after scattering is minimal.

The effects of multiply scattered light can be reduced also by using a polarizer. A polarizer only allows the fibers to accept a portion of the unpolarized light thus reducing the sensitivity of the cross-correlation function to multiple scattering.

In addition to restricting the observed scattering region with optical stops, lenses, etc., another obvious improvement to the geometry is to use a much more strongly focused incident beam. The focusing of the incident beam increases the size of the single scattering speckles and allows the advantage of greater separation of the fiber cores. This arrangement also increases the size of the region from which multiple scattering can arise, thus reducing the size of multiple scattering speckles and their contribution to the cross-correlation function. In addition, the dramatic reduction of the signal amplitude to baseline ratio for the cross-correlation function as multiple scattering becomes significant, can be used to determine the ratio of singly to multiple scattering. The square root of the amplitude to baseline ratio is proportional to the ratio of the single scattering to the total scattered power, provided the fibers are far enough apart to yield negligible cross-correlation from multiple scattering. Combining the cross-correlation signal amplitude to baseline ratio with a direct measurement of the total scattering allows for measurements of the single scattering cross section, even for highly turbid media.

The ability to make reasonable easily interpretable dynamic light scattering measurements on strongly scattering samples is valuable in both basic research and industrial applications. Examples of research areas where multiple scattering is significant, and measurements currently difficult, include the study of particle dynamics in strongly interacting systems, critical point phenomenon and in VIVO biological and medical studies. Examples of the many industrial application include the characterization of various slurries for use for grinding and polishing, paint particle studies, sizing of particles in concentrated suspensions, and quality control particles which may involve colloidal intermediate stages.

The invention has been described with reference to a preferred embodiment and alternatives thereof. It is believed that many modifications and alterations to the embodiments disclosed will readily suggest themselves to those skilled in the art upon reading and understanding the detailed description of the invention. The invention is intended to include all such modifications and alterations insofar as they come within the scope of the present invention.

Having thus described the invention, it is claimed:

1. An apparatus for analyzing a fluid containing particles comprising a light source to direct a beam of light which intersects said fluid, a focuser to converge said light beam to a focal waist in said fluid, a plurality of detectors spaced from said fluid to receive at least a portion of said light beam scattered by said fluid, said plurality of detectors positioned to detect substantially single scattered light, and a data processor, said plurality of detectors sending signals to said data processor when said scattered light is detected, said data processor cross-correlating said signals received from said plurality of detectors to at least minimize multiple scattering effects from said light beam scattered by said fluid.

2. An apparatus as defined in claim 1, including a fluid container having a polished surface to reduce distortion of said laser beam.

3. An apparatus as defined in claim 2, including an index matching container containing an index matching fluid, said fluid container being positioned in said index matching container.

4. An apparatus as defined in claim 3, wherein said index matching container includes a polished surface to reduce distortion of said laser beam.

5. An apparatus as defined in claim 4, wherein said plurality of detectors are substantially aligned on said focal waist.

6. An apparatus as defined in claim 5, wherein said plurality of detectors lie at a scattering angle of greater than 0° relative to a direction of propagation of said beam of light.

7. An apparatus as defined by claim 6, wherein said plurality of detectors spaced at a substantially equal distance from said focal waist.

8. An apparatus as defined in claim 7, wherein said data processor calculates the average particle size of said particles in said fluid.

9. An apparatus as defined in claim 8, including a polarizer positioned between said focal waist and at least one of said detectors to block a substantial amount of multiple scattered light.

10. An apparatus as defined in claim 9, wherein said plurality of detectors positioned within a single speckle of said scattered light.

11. An apparatus as defined in claim 1, wherein said plurality of detectors are substantially aligned on said focal waist.

12. An apparatus as defined in claim 1, wherein said plurality of detectors lie at a scattering angle of greater than 0° relative to a direction of propagation of said beam of light.

13. An apparatus as defined by claim 1, wherein said plurality of detectors spaced at a substantially equal distance from said focal waist.

14. An apparatus as defined in claim 1, wherein said data processor calculates the average particle size of said particles in said fluid.

15. An apparatus as defined in claim 1, including a polarizer positioned between said focal waist and at least one of said detectors to block a substantial amount of multiple scattered light.

16. An apparatus as defined in claim 1, wherein said plurality of detectors positioned within a single speckle of said scattered light.

17. An apparatus for analyzing a fluid containing particles comprising a wave source directed into said fluid to create scattered waves, a detector arrangement to detect at least a portion of said scattered waves at least two distinct locations, and an analyzer to analyze received scattered waves to determine at least one physical property of said particles in said fluid, said detector arrangement including at least two detectors spaced from said fluid, said detected scattered waves being substantially singly scattered waves, said analyzer minimizing multiple scattering effects from said received scattered wave.

18. An apparatus as defined in claim 17, including a focuser to converge said wave source to a narrow focal waist in said fluid.

19. An apparatus as defined in claim 18, wherein said at least two detectors being substantially aligned on said focal waist.

20. An apparatus as defined by claim 19, wherein said at least two detectors spaced at a substantially equal distance from said focal waist.

21. An apparatus as defined in claim 20, wherein said detectors being oriented at substantially a same angle to said focal waist.

22. An apparatus as defined in claim 21, including a polarizer positioned between said focal waist and at least one of said detectors.

23. An apparatus as defined in claim 22, wherein said wave source is a laser beam.

24. An apparatus as defined in claim 23, wherein said determined physical property of said particle is the average particle size of said particle in said fluid.

25. An apparatus as defined in claim 19, wherein said detectors being oriented at substantially a same angle to said focal waist.

26. An apparatus as defined in claim 19, including a polarizer positioned between said focal waist and at least one of said detectors.

27. An optical method of analyzing a fluid having particles which scatters a wave source when directed through said fluid comprising the steps of:
   a. generating a wave source;
   b. exposing said fluid to said wave source to produce scattered waves;
   c. detecting at least a portion of said scattered waves at a plurality of regions, said step of detecting including the detecting of substantially singly scattered waves; and
   d. analyzing said detected scattered wave source to determine a physical property of said particles in said fluid, said step of analyzing including cross-correlating said detected scattered wave source to minimize the effects of multiply scattered waves.

28. The method as defined in claim 27, wherein said step of detecting including at least two detectors, each of said detectors positioned at one of said regions.

29. The method as defined in claim 28, wherein at least two of said detectors being positioned within a single speckle.

30. The method as defined in claim 29, including the step of focusing said wave source to converge said wave source to a narrow focal waist in said fluid.

31. The method as defined in claim 30, including the step of aligning each of said detectors substantially at said focal waist.

32. The method as defined in claim 31, wherein said detectors spaced at a substantially equal distance from a focal waist.

33. The method as defined in claim 32, wherein said wave source is a laser beam.

34. The method as defined in claim 33, wherein said determined physical property includes the average particle size of particles in said fluid.

35. The method as defined in claim 34, wherein said wave source is focused by a device selected from the group consisting of a lens, a mirror and combinations thereof.

36. The method as defined in claim 35, wherein said detectors includes an optical fiber.

37. The method as defined in claim 27, including the step of focusing said wave source to converge said wave source to a narrow focal waist in said fluid.

38. The method as defined in claim 37, including the step of aligning each of said detectors substantially at said focal waist.

39. An apparatus for analyzing a fluid containing particles comprising a light source to direct a beam of light at said fluid, said light substantially traveling along a light axis, a plurality of detectors spaced from said fluid and positioned at an angle from said light axis, and a data processor, said plurality of detectors receiving at least a portion of said light beam scattered by said fluid and sending signals to said data processor when at least a portion of said light beam is detected, said plurality of detectors spaced from one another such that one of said detectors receives scattered light scattered in a direction different from said scattered light received by another of said detectors, said data processor cross-correlates said signals received from said plurality of detectors to discriminate single scattering and multiple scattering of said detected scattered light and to determine a physical property of the fluid, said physical property includes the average particle size of particles in said fluid.

40. An apparatus as defined in claim 39, including a focuser to converge said light beam to a focal waist in said fluid.

41. An apparatus as defined in claim 40, including an index matching container to hold said fluid container, said index matching container including a polished surface reduce distortion of said light beam and said scattered light.

42. An apparatus as defined in claim 40, wherein detectors lie at a scattering angle of greater than 0° relative to said light axis.

43. An apparatus as defined by claim 42, wherein said detectors spaced at a substantially equal distance from said focal waist.

44. An apparatus as defined in claim 43, including a polarizer positioned between said focal waist and at least one of said detectors.

45. An apparatus as defined in claim 44, wherein said plurality of detectors positioned within a single speckle of said scattered light.

\* \* \* \* \*

UNITED STATES PATENT AND TRADEMARK OFFICE
CERTIFICATE OF CORRECTION

PATENT NO. : 5,956,139
DATED : September 21, 1999
INVENTOR(S) : William V. Meyer; David S. Cannell; Padetha Tin; H. Michael Cheung; J. Adin Mann, Jr.; Thomas W. Taylor; James A. Lock; Jixiang Zhu; and Anthony E. Smart It is certified that error appears in the above-identified patent and that said Letters Patent is hereby corrected as shown below:

Column 1, line 17 insert the following --This invention was made with Government support under contract awarded by NASA. The Government has certain rights in this invention.--.

Signed and Sealed this

Twenty-seventh Day of March, 2001

*Attest:*

NICHOLAS P. GODICI

*Attesting Officer*  *Acting Director of the United States Patent and Trademark Office*